United States Patent [19]
Wallace et al.

[11] Patent Number: 6,074,399
[45] Date of Patent: Jun. 13, 2000

[54] HAND-HELD FETAL VACUUM EXTRACTOR HAVING AN INTEGRATED PUMP AND HANDLE

[75] Inventors: William Dean Wallace; Richard A. Dixon; Steven R. Smith, all of Salt Lake City; Christopher A. Cutler, Centerville, all of Utah

[73] Assignee: Clinical Innovations, Salt Lake City, Utah

[21] Appl. No.: 09/075,448

[22] Filed: May 8, 1998

[51] Int. Cl.[7] ................................................ A61B 17/42
[52] U.S. Cl. ............................................ 606/123; 606/122
[58] Field of Search .................................. 606/122, 123; 604/73, 149

[56] References Cited

U.S. PATENT DOCUMENTS

| | | | |
|---|---|---|---|
| 2,194,989 | 3/1940 | Torpin | 128/361 |
| 2,702,038 | 2/1955 | Uddenberg et al. | 128/361 |
| 2,917,050 | 12/1959 | Kenyon | 128/361 |
| 3,202,152 | 8/1965 | Wood et al. | 128/361 |
| 3,207,160 | 9/1965 | Heyns | 128/361 |
| 3,612,722 | 10/1971 | Neward | 417/63 |
| 3,765,408 | 10/1973 | Kawai | 128/352 |
| 3,782,385 | 1/1974 | Loyd | 128/281 |
| 3,794,044 | 2/1974 | Vennard et al. | 128/352 |
| 5,019,086 | 5/1991 | Neward | 606/123 |
| 5,071,403 | 12/1991 | Larsson | 604/74 |
| 5,224,947 | 7/1993 | Cooper et al. | 606/123 |
| 5,281,229 | 1/1994 | Neward | 606/123 |

FOREIGN PATENT DOCUMENTS

| | | |
|---|---|---|
| 1123432 | 2/1962 | Germany . |
| 3138-589 | 7/1975 | Germany . |
| 61B17/42 | 3/1955 | Sweden . |
| WO89/06112 | 7/1989 | WIPO . |

OTHER PUBLICATIONS

CMI Obstetrical Vacuum Delivery Kit product information, Aug. 1995, Redmond, Oregon, 34 pages.

Handbook of Vacuum Extraction in Obstetric Practice, Aldo Vacca, pp. 55–62.

Chapter 9, Vacuum Delivery, Operative Obstetrics, pp. 173–189.

Arvind S. Moolgaoker, MD, SYED O.S. Ahamed, and Peter R. Payne, A Comparison of Different Methods of Instrumental Delivery Based on Electronic Measurements of Compression and Traction, Feb. 19, 1979, pp. 1–4.

*Primary Examiner*—Michael Buiz
*Assistant Examiner*—Kevin Truong
*Attorney, Agent, or Firm*—Workman, Nydegger & Seeley

[57] ABSTRACT

A hand-held fetal vacuum extractor combines a pump and handle into a single hand-held unit. This enables a single operator, such as a doctor, to control vacuum using a vacuum pump, and apply traction to a fetus using a single hand. A handle, having a surface for gripping, is connected to a fetal vacuum cup for being suctioned onto a fetal head. A vacuum pump is connected to the handle and includes an activation surface for activating the vacuum pump. The vacuum pump is fluidly coupled to a the vacuum cup and fetal head. The grip surface of the handle and the activation surface of the pump are in such proximity, during operation, that a single human hand can simultaneously grasp the grip surface and contact the activation surface.

35 Claims, 10 Drawing Sheets

HAND-HELD FETAL VACUUM EXTRACTOR HAVING AN INTEGRATED PUMP AND HANDLE

BACKGROUND OF THE INVENTION

The safe propagation of the human race is fundamental to the well being of our society. One need not be a parent to realize the importance of improved medical devices and methods in delivering a fetus safely into this world. Currently, there are two major methods for delivering a fetus, the Cesarean section delivery and the vaginal delivery.

In Cesarean section deliveries, the fetus is delivered through an incision made in the uterus and a corresponding incision made in the abdomen. An upward pulling force is required in order to pull the fetus through the incisions and out of the mother. Often the force is provided by the doctor's hands directly pulling the fetus through the abdominal incision.

In vaginal deliveries, the fetus is delivered through the vaginal passage after the cervix has fully dilated and effaced. Passing the fetus through the vaginal passage requires that the vaginal muscles be forced to stretch because the fetal head is much larger than the vaginal passage under normal circumstances.

Some stretching force is applied to the vaginal tissues by the mother herself. The involuntary contractions of the uterus during labor push the fetus (typically the fetal head) into the vaginal passage to stretch the vaginal tissues. The stretching force of these involuntary uterine contractions is combined with the stretching force caused by voluntary contractions of the mother's abdominal muscles as the mother tries to push the fetus out of the uterus.

Often the forces described above are not strong enough or are not medically advisable to use in extracting the fetus. Supplementary force may be applied with a fetal vacuum extractor, for example, in conditions of dystocia (i.e., slow or difficult labor or delivery), uterine inertia, maternal exhaustion, maternal distress, or fetal distress.

In a conventional fetal vacuum extractor, a vacuum cup is sealed over a portion of the fetal head (e.g., the occiput). A flexible tube connects the vacuum cup to a vacuum pump operated by a secondary operator such as a nurse. The vacuum pump allows the nurse to provide a vacuum within the vacuum cup thereby creating suction between the fetal head and the vacuum cup. As long as a sufficient vacuum is maintained, the primary operator, such as a doctor, may pull on the vacuum cup handle thereby applying traction (i.e., a pulling, delivering force) to the fetal head.

Bodily fluids on the fetal head assist in making a seal between the fetal head and the vacuum cup to define a chamber. However, the vacuum is often unintentionally released as fluid seeps against the normal flow of a one-way valve provided in the vacuum pump. Vacuum is also unintentionally released when the seal between the fetal head and vacuum cup is broken. In order to minimize the chances of fetal injury, the vacuum is intentionally lowered between contractions or when the vacuum is determined to be too strong. Therefore, the vacuum must be constantly monitored and adjusted, and must have a method to release or lower the vacuum.

The conventional fetal vacuum extractor is designed so that the doctor pulls on the handle to provide traction while the nurse monitors and adjusts the vacuum. The doctor instructs the nurse to provide more (or less) vacuum when the doctor determines that the vacuum is too weak (or too strong).

Unfortunately, time elapses between the time the doctor determines that a vacuum is needed and the time a vacuum is provided. This time includes the time required for a doctor to issue oral instructions after the doctor has determined that a vacuum adjustment is needed, and the time required for a nurse to respond to the oral instructions. Typically, this time is only a matter of seconds. However, because the vacuum may be lost very quickly, this additional response time may cause disengagement of the vacuum cup with the fetal head, interrupting the delivery. If the vacuum is too strong, this additional response time may cause injury to the fetal head.

The conventional fetal vacuum extractor also has a relatively large volume of fluid that is sealed off during the vacuuming operation. Therefore, more fluid must be pumped out of the sealed volume in order to maintain a given vacuum compared to a system in which the sealed off fluid volume is less.

Therefore, what is desired is a fetal vacuum extractor in which a single operator, such as a doctor, can conveniently and directly control the vacuum within the vacuum cup at the same time as pulling or applying force to the vacuum cup. Furthermore, a fetal vacuum extractor having a relatively low sealed off fluid volume is desired because the vacuum can be created faster with fewer pumps and with a smaller, more compact pump.

SUMMARY OF THE INVENTION

A fetal vacuum extractor is provided which combines a pump and handle into a single hand-held unit. This enables a single operator to, with one hand, both control a vacuum in an attached vacuum cup using a vacuum pump, and apply traction to a fetus.

The fetal vacuum extractor has a vacuum cup having a cup portion defining a cup chamber for application to a fetus. A handle, which includes a grip surface, is connected to the fetal vacuum cup so that the fetal vacuum cup can be maneuvered. A vacuum pump has at least a portion (e.g., a piston) rigidly connected to the handle and includes an activation surface for activating the vacuum pump. The grip surface of the handle and the activation surface of the pump are in such proximity, during operation, that a single human hand can simultaneously grip the grip surface and contact the activation surface. The fetal vacuum extractor is operated by simultaneously gripping the handle with a hand and activating the vacuum pump with the same hand.

In one embodiment, the vacuum pump defines a chamber surface with a piston attached to the handle. The vacuum pump is slidable relative to the handle and piston. Compression of the activation surface of the vacuum pump relative to the handle causes the piston to exhaust fluid through a valve into the atmosphere. During decompression, fluid is drawn into the vacuum chamber to create a vacuum when there is a seal of the cup portion with a fetal head. The principles of the invention are described in more detail below.

DETAILED DESCRIPTION OF THE INVENTION

The present invention includes a hand-held fetal vacuum extractor and method that has a cup which attaches to the fetal head, a handle connected to the cup for applying traction to the fetus, and a vacuum pump built into the handle. The fetal vacuum extractor combines the handle and vacuum pump into a single hand-held unit. A vacuum indicator and vacuum release mechanism may also be integrated into the hand-held fetal vacuum extractor. This enables a single operator to apply traction and adjust the vacuum in the cup using a single hand. The other hand is left free to perform other essential functions (e.g., guiding the fetal head, or suctioning the fetal nose and mouth). Furthermore, the vacuum indicator may be positioned to be visible to the single operator to give the operator guidance in adjusting the vacuum in the cup in a timely manner.

While the fetal vacuum extractor of the present invention is described with respect to the following specific embodiments, these embodiments are illustrative only, and not limiting. Throughout this description, like symbols in different figures indicate the same or similar elements. Reference axes are also shown in all of the figures.

Figure 1:
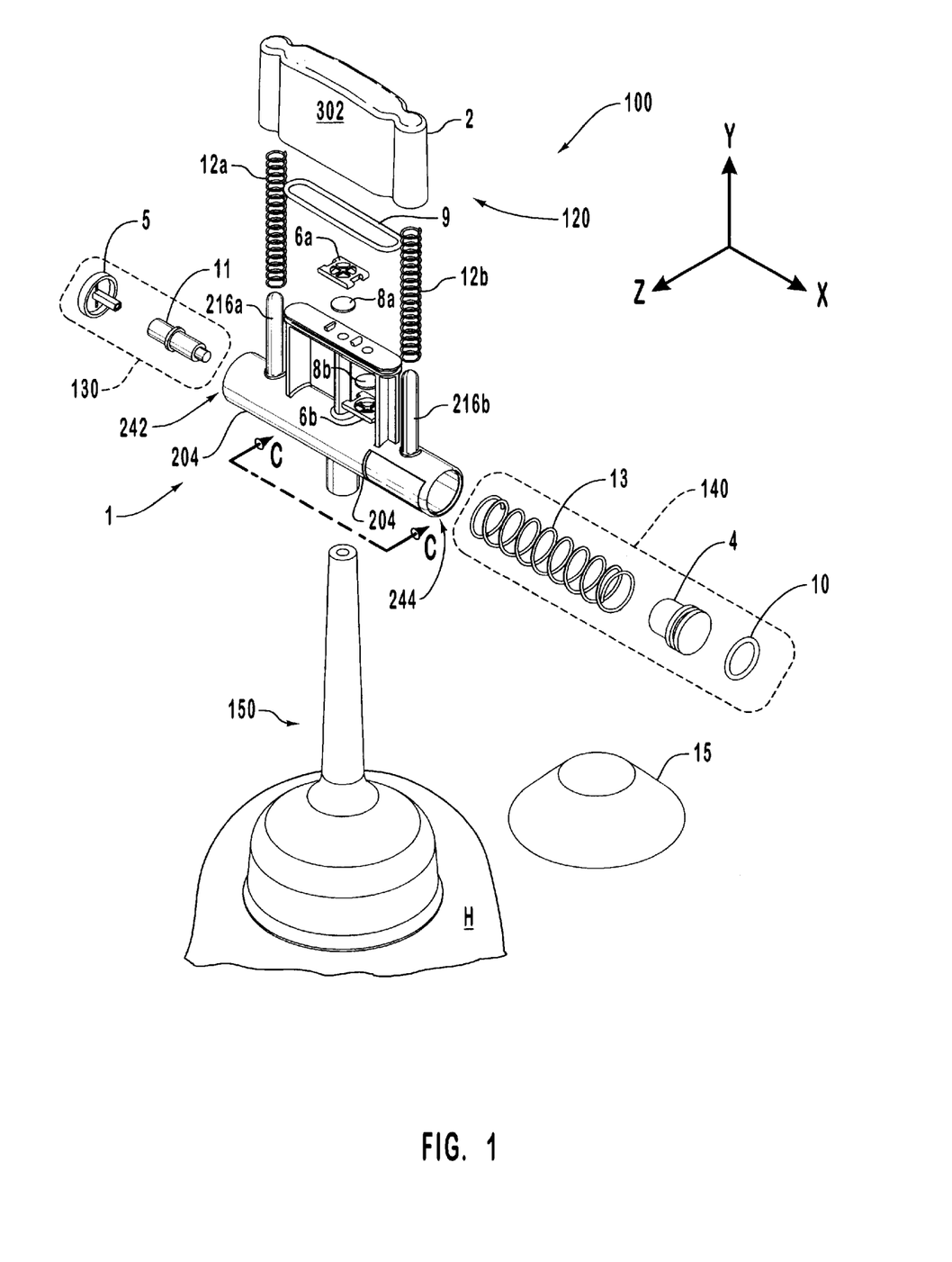
FIG. 1 is an exploded isometric view of one embodiment of a fetal vacuum extractor according to the invention.

FIG. 1 is an exploded isometric view of a fetal vacuum extractor 100 according to the invention. Extractor 100 includes five general components: a handle 1, a vacuum pump 120, a vacuum release 130, a vacuum indicator 140, and a vacuum cup 150. The pumping action of the extractor 100 is caused by the relative movement between handle 1 and palm chamber 2 (or vacuum pump 120).

First, the structure of handle 1, of palm chamber 2, and of the interconnection between handle 1 and palm chamber 2 are described. Second, the pumping action between handle 1 and palm chamber 2 is described. Third, the vacuum release 130, vacuum indicator 140, and vacuum cup 150 are described. Finally, various alternative embodiments are described.

Figure 2A:
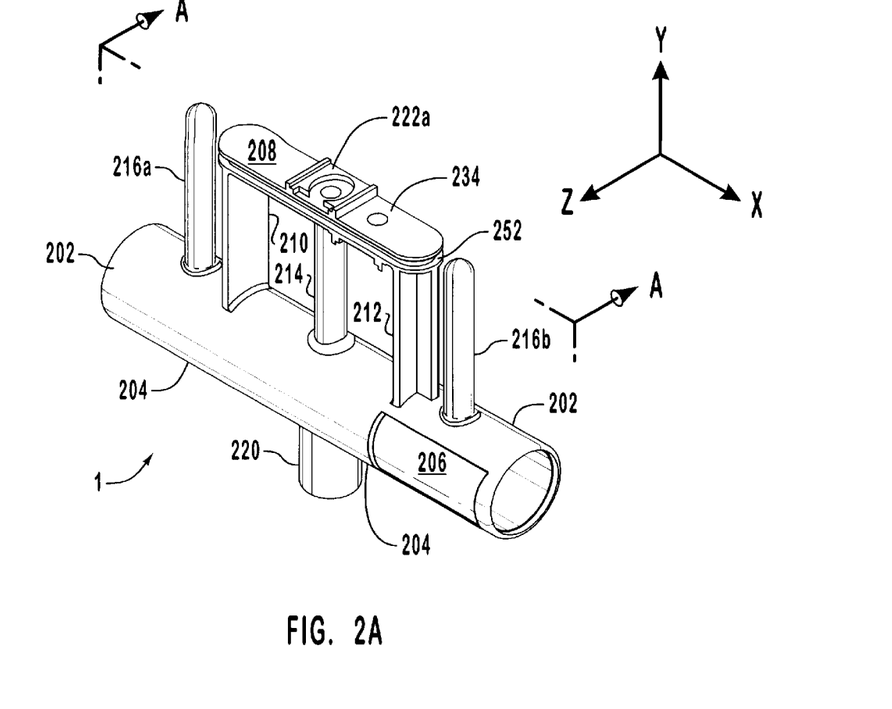
FIG. 2A is an isometric view of the handle of FIG. 1.

The structure of handle 1 is now described. FIG. 2A is an isometric view of handle 1. Handle 1 may be machined or molded and may be composed of polycarbonate or some other plastic. Handle 1 includes a main grip 202 having a grip surface 204 and a vacuum indicator window 206. A piston 208 is part of vacuum pump 120 but is rigidly connected to handle 1. Piston 208 extends up from main grip 202 and is supported by side supports 210 and 212 and central support 214. Two spring guide columns 216a and 216b also extend up from main grip 202. A cup connector 220 extends down from main grip 202. Piston 208 has a top vacuum chamber surface 234 that defines upper flap recess 222a for receiving a one-way vacuum flap valve 8a (FIG. 1) composed of, for example, silicone.

Figure 2B:
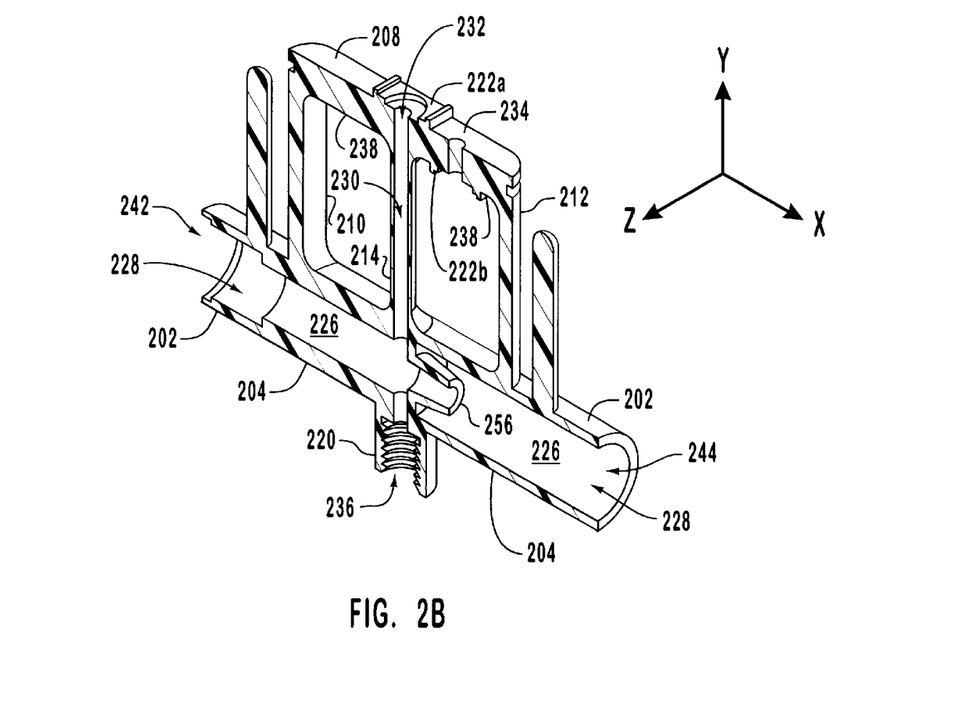
FIG. 2B is an isometric sectional view of the handle of FIG. 2A along cutting plane A—A of FIG. 2A.

FIG. 2B is an isometric cross sectional view of handle 1 along cutting plane A—A of FIG. 2A. FIG. 2B shows a lower flap recess 222b provided in a lower surface 238 of piston 208 for receiving a one-way exhaust flap valve 8b (FIG. 1) composed of, for example, silicone. Main grip 202 is hollow having an inner surface 226 that defines a grip chamber 228. The grip chamber 228 is substantially sealed from atmosphere during operation as described in detail below. Central support 214 is hollow having an internal vacuum source channel 230 connecting grip chamber 228 to a hole 232 at the top chamber surface 234 of piston 208. Cup connector 220 is also hollow having an internal channel 236 having a top end coupled to grip chamber 228.

Figure 3A:
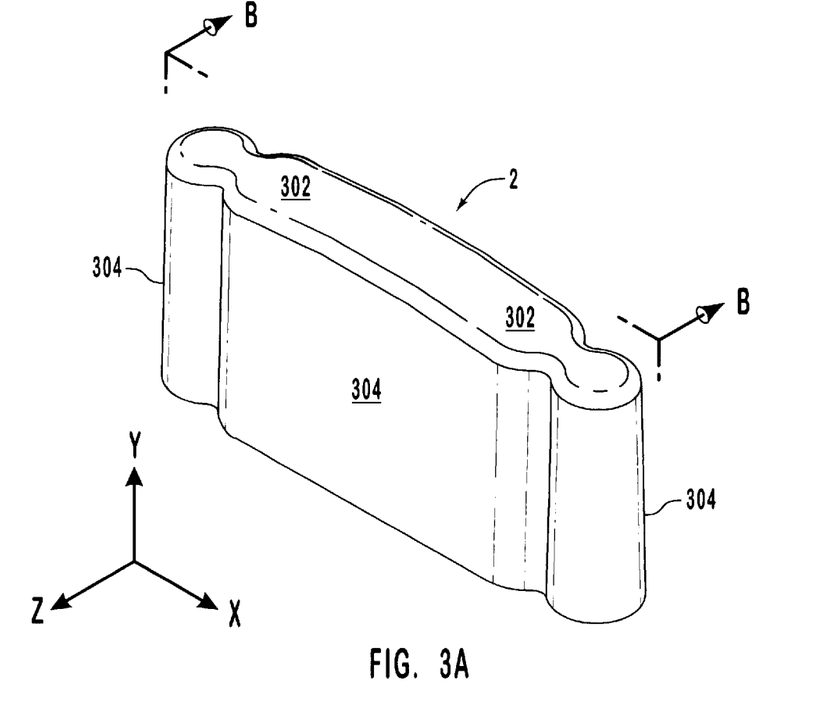
FIG. 3A is an isometric view of the palm chamber of FIG. 1.
Figure 3B:
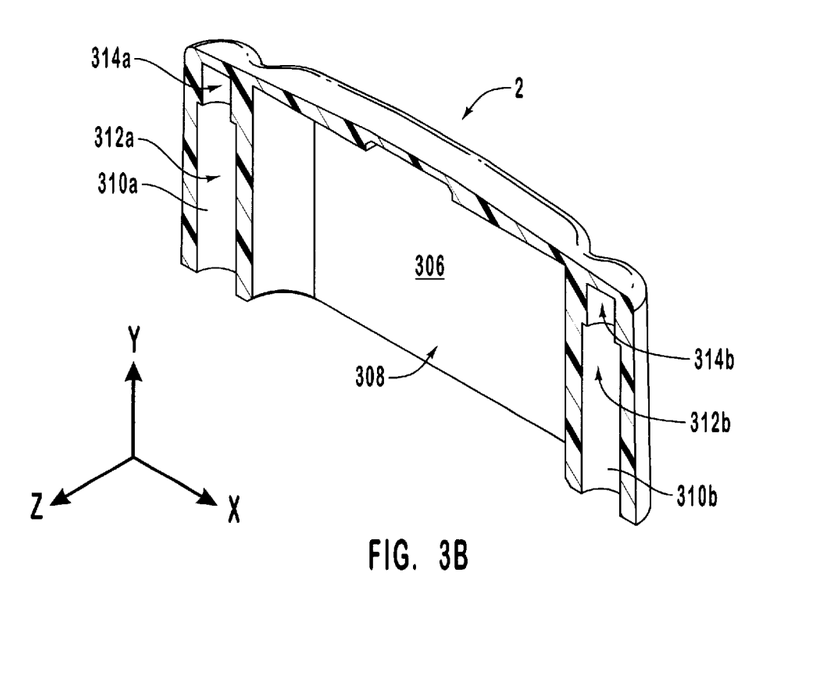
FIG. 3B is an isometric sectional view of the palm chamber of FIG. 3A along cutting plane B—B of FIG. 3A.

The structure of palm chamber 2 is now described. Palm chamber 2 (part of vacuum pump 120) may be machined and/or molded, and may be composed of polyethylene or similar plastics. Palm chamber 2 is disposed over piston 208 and is described with reference to FIG. 3A and FIG. 3B. FIG. 3A is an isometric view of palm chamber 2 that is one integrated body having an upper activation surface 302 and a side surface 304. FIG. 3B is an isometric sectional view of palm chamber 2 along cutting plane B—B of FIG. 3A. FIG. 3B shows that palm chamber 2 has an inner chamber surface 306 that, together with vacuum o-ring 9 (FIG. 1) and top chamber surface 234 of piston 208, defines a vacuum chamber 308.

Fluid may be vacuumed from internal vacuum source channel 230 into vacuum chamber 308 through one-way vacuum flap valve 8a provided in vacuum flap recess 222a. Fluid may be exhausted from vacuum chamber 308 through one-way exhaust flap valve 8b provided in exhaust flap recess 222b.

Palm chamber 2 also has inner guide surface 310a (and 310b) which defines a large diameter bore 312a (and 312b) and a small diameter bore 314a (and 314b). In its assembled, uncompressed position, compression springs 12a and 12b are received into respective large diameter bores 312a and 312b, but are not received into small diameter bores 314a and 314b.

The structure of the interconnection between handle 1 and palm chamber 2 is now described. Referring again to FIG. 1, vacuum pump 120 includes compression springs 12a and 12b (composed of, for example, stainless steel) which are fitted over respective spring guide columns 216a and 216b. Vacuum and exhaust flap valves 8a and 8b are fitted into the respective upper and lower recesses 222a and 222b. Vacuum and exhaust retaining rings 6a and 6b (composed of, for example, nylon or polycarbonate) are fitted into respective flap recesses 222a and 222b over respective flap valves 8a and 8b. A vacuum o-ring 9 (composed of, for example, silicone) is positioned along an outer periphery surface of piston 208 within groove 252 (FIG. 2A).

The pumping action of vacuum pump 120 between handle 1 and palm chamber 2 is now described. When palm chamber 2 is compressed downward (in the negative y-direction parallel to the y-axis) with respect to handle 1, compression springs 12a and 12b are compressed by the end of respective large diameter bores 312a and 312b at one end. Compression springs 12a and 12b are compressed at the opposite end by the main grip 202. Therefore, extractor 100 is biased towards an uncompressed position. In the assembled, uncompressed position of extractor 100, approximately three inches separates activation surface 302 of palm chamber 2 and grip surface 204 of main grip 202 such that the fingers of an average human hand can simultaneously grip main grip 202 at grip surface 204 and press on palm chamber 2 at activation surface 302. However, this distance can vary from one inch or less to five inches or more to accommodate different hand sizes and gripping preferences.

Figure 5A:
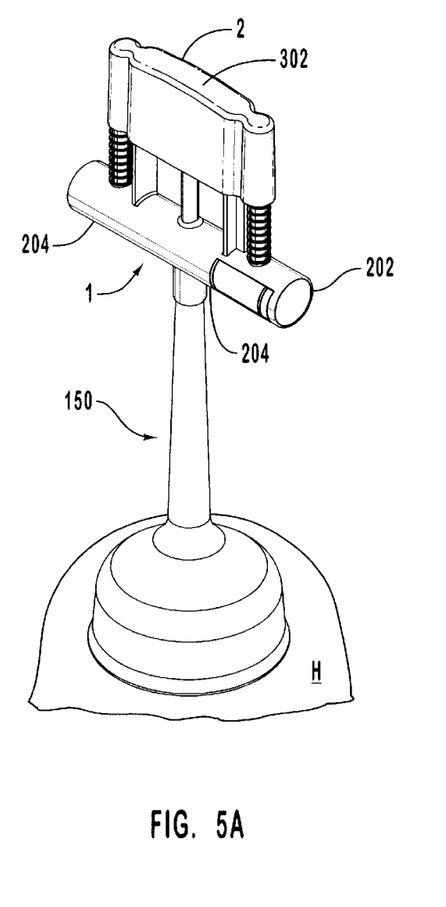
FIG. 5A is an isometric view of the fetal vacuum extractor of FIG. 1 in its assembled, uncompressed position.

An operator pumps the extractor 100 by gripping the extractor 100 in its assembled, uncompressed position shown in FIG. 5A. The fingers of the operating hand are placed around main grip 202 while placing the palm of the operating hand is pressed against the activation surface 302 of the palm chamber 2. The operator squeezes the fingers towards the palm, thereby overcoming the bias of compression springs 12a and 12b towards the uncompressed position. As the fingers and palm are squeezed towards each other, palm chamber 2 is pressed towards handle 1.

Figure 5B:
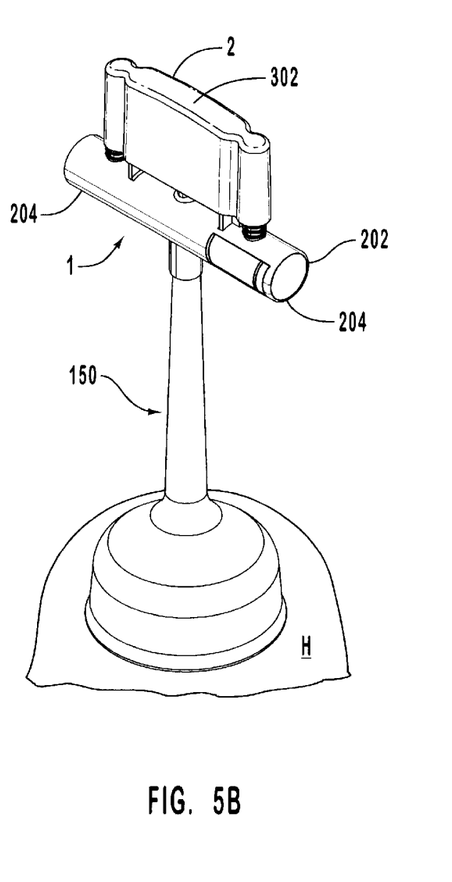
FIG. 5B is an isometric view of the fetal vacuum extractor of FIG. 1 in its assembled, compressed position.

The movement of piston 208 relative to palm chamber 2 forces piston 208 into vacuum chamber 308 and decreases the volume of vacuum chamber 308. The pressure within vacuum chamber 308 increases above the ambient pressure just enough to open the one-way exhaust flap valve 8b to exhaust the fluid from vacuum chamber 308 as palm chamber 2 is compressed. During compression, the pressure within vacuum chamber 308 only slightly rises above the ambient pressure enough to keep the one-way exhaust flap valve 8b open. Essentially, the pressure within vacuum chamber 308 is at ambient pressure during compression of palm chamber 2. In the assembled, compressed position of extractor 100 (shown in FIG. 5B), the distance between activation surface 302 of palm chamber 2 and grip surface 204 of main grip 202 is approximately two inches, but may vary from a half inch or less to four inches or more.

After the palm chamber 2 is compressed, the operator stops applying compressive force with the palm. Compression springs 12a and 12b then urge extractor 100 towards its uncompressed position. The decompressing movement between piston 208 and palm chamber 2 causes the one-way vacuum flap valve 8a to open when the pressure of vacuum chamber 308 drops below the pressure within vacuum source channel 230. Thus the decompression movement causes fluid from grip chamber to be vacuumed into vacuum chamber 308.

Vacuum release 130 is now described with reference to FIG. 1. A vacuum release 130 is provided in one longitudinal end 242 of main grip 202 to cap one end of grip chamber 228. Vacuum release 130 includes a release valve 11 (composed of, for example, polyester, PVC, and/or stainless steel) which is first inserted into the end 242 of main grip 202. Release valve 11 may be, for example, part number BK333303S supplied by Bestak of Norfork, England. Vacuum release 130 also includes a release button 5 (composed of, for example, polycarbonate) which is inserted into the end of main grip over release valve 11. When release button 5 is pressed by, for example, the operator's thumb, fluid within grip chamber 228 communicates with the ambient environment through release value 11. If there is a vacuum within grip chamber 302 with respect to the ambient pressure, the vacuum is released when release button 5 is pressed.

Vacuum indicator 140 is now described with reference to FIG. 1. A vacuum indicator 140 is provided in the other longitudinal end 244 of main grip 202 and caps the other longitudinal end of grip chamber 228. The vacuum indicator 140 includes a gauge spring 13, a gauge ring 4 (composed of, for example, polycarbonate) and a gauge o-ring 10 (composed of, for example, silicone). The gauge o-ring 10 is provided within a groove along the outer circumference of gauge ring 4 so that gauge ring 4 acts as a seal between grip chamber 228 and the ambient environment. Gauge ring 4 is free to slide along a longitudinal direction (i.e., parallel to the x-axis) within grip chamber 228 in response to pressure differences between grip chamber 228 and the ambient pressure. Gauge ring 4 compresses gauge spring 13 substantially proportional to the vacuum level within grip chamber 228. A scale is provided on main grip 202 which correlates the position of the gauge ring 4 with the pressure within grip chamber 228. For example, the position of gauge ring 4 at a vacuum of 58 centimeters of mercury is marked on the scale with "58".

Figure 7A:
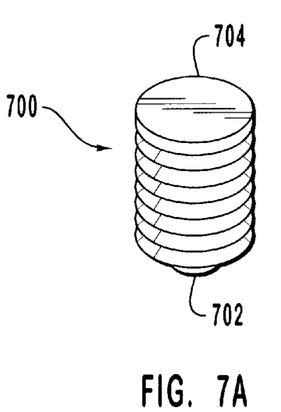
FIG. 7A shows a vacuum indicator bellows in a contracted state.
Figure 7B:
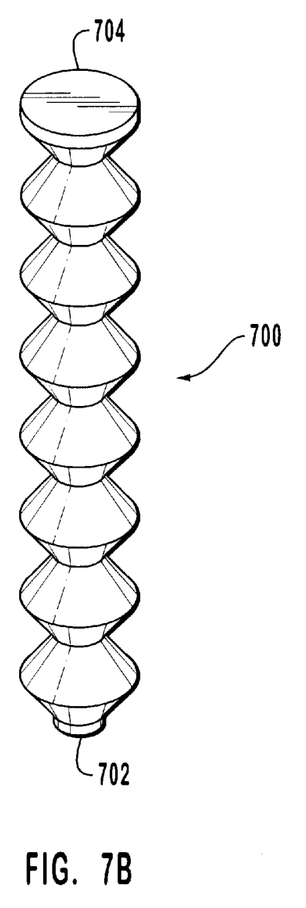
FIG. 7B shows the vacuum indicator bellows in an expanded state.

Alternatively, vacuum indicator 140 may be composed of a bellows 700 (FIG. 7A and FIG. 7B) having an open end 702 and a sealed end 704. Open end 702 is seated over bellows attachment 256 (FIG. 2B). Bellows 700 expands (and contracts) in response to a weaker (and stronger) vacuum within grip chamber 228. Therefore, the position of a given part of bellows 700 (e.g., sealed end 704) is an indicator of the vacuum within grip chamber 228. FIG. 7A shows bellows 700 in a contracted state while FIG. 7B shows bellows 700 in an expanded state.

Vacuum release 130 and vacuum indicator 140 cap both ends 242 and 244 of grip chamber 228 so that when vacuum release 130 is not activated and vacuum flap valve 8a is closed, the grip chamber 308 and vacuum source channel 230 combination are sealed off except through channel 236.

Figure 4:
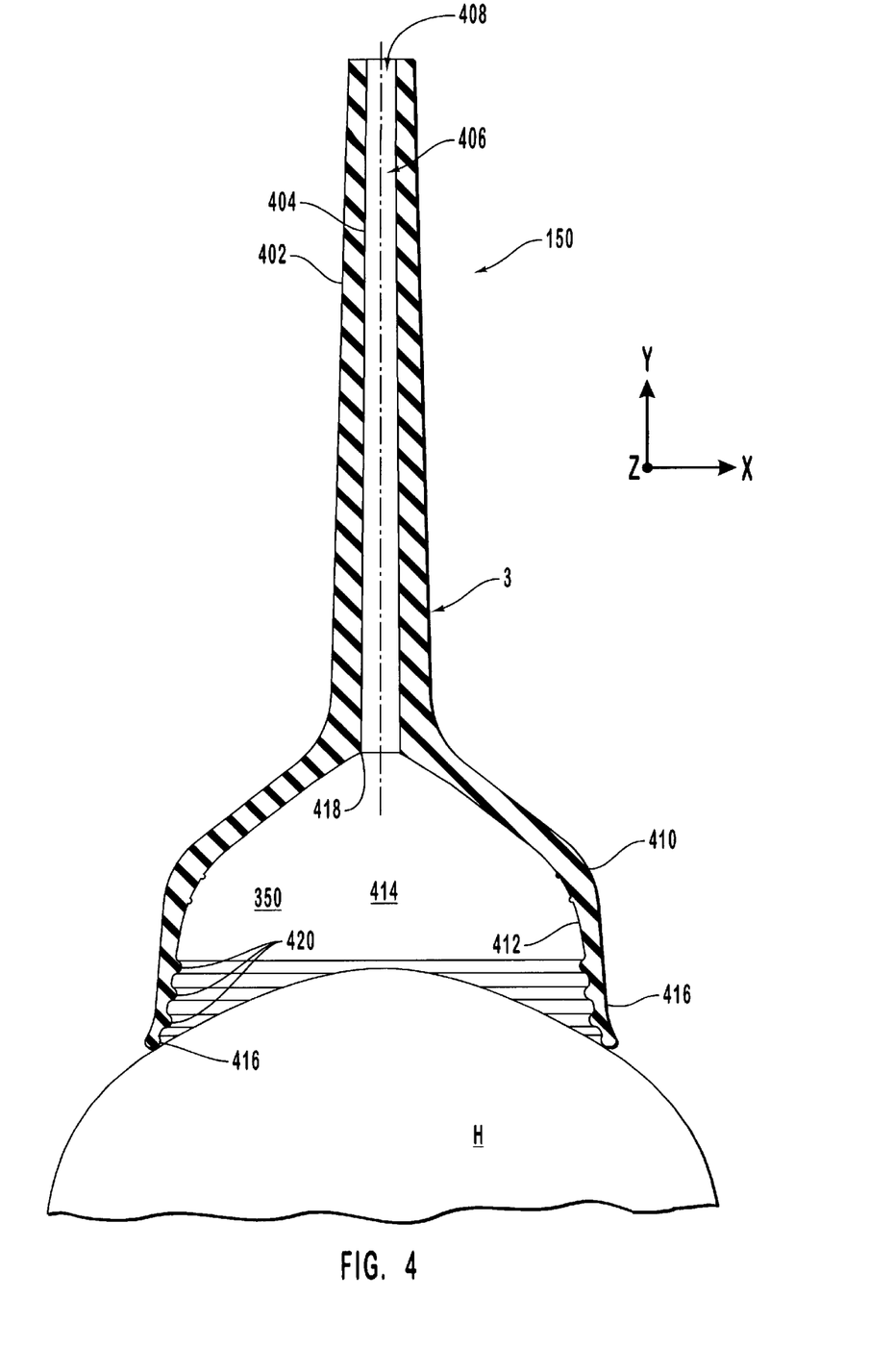
FIG. 4 is a cross sectional diagram the vacuum cup of FIG. 1 along cutting plane C—C of FIG. 1.

Vacuum cup 150 is now described with reference to FIG. 4. FIG. 4 shows that vacuum cup 150 includes a cup 3 that is shown along cutting plane C—C of FIG. 1. Cup 3 may be molded or vacuum formed and is composed of a flexible material such as silicone, Kraton, or polyethylene. Cup 3 is semi-rigid and includes a hollow shaft 402 having an inner wall 404 defining a cup channel 406. "Semi-rigid" is defined as "able to hold its shape and yet may be capable of flexing."

Hollow shaft 402 may be approximately five inches long, but may range from three inches long or less to seven inches long or more depending on the preference of the primary operator, the type of birth opening (e.g., Cesarean incision), and the anatomy of the mother. One end 408 of shaft 402 is tightly connected to channel 236 of handle 1 so that grip chamber 228 is fluidly coupled to cup channel 406. Vacuum cup 150 also includes a flexible cup portion 410 having an inner wall 412 to define a cup chamber 414. Cup chamber 414 is fluidly coupled to cup channel 406 at an apex 418. Cup portion 410 has a lip 416 that contacts the work piece (e.g., fetal head H).

Figure 8:
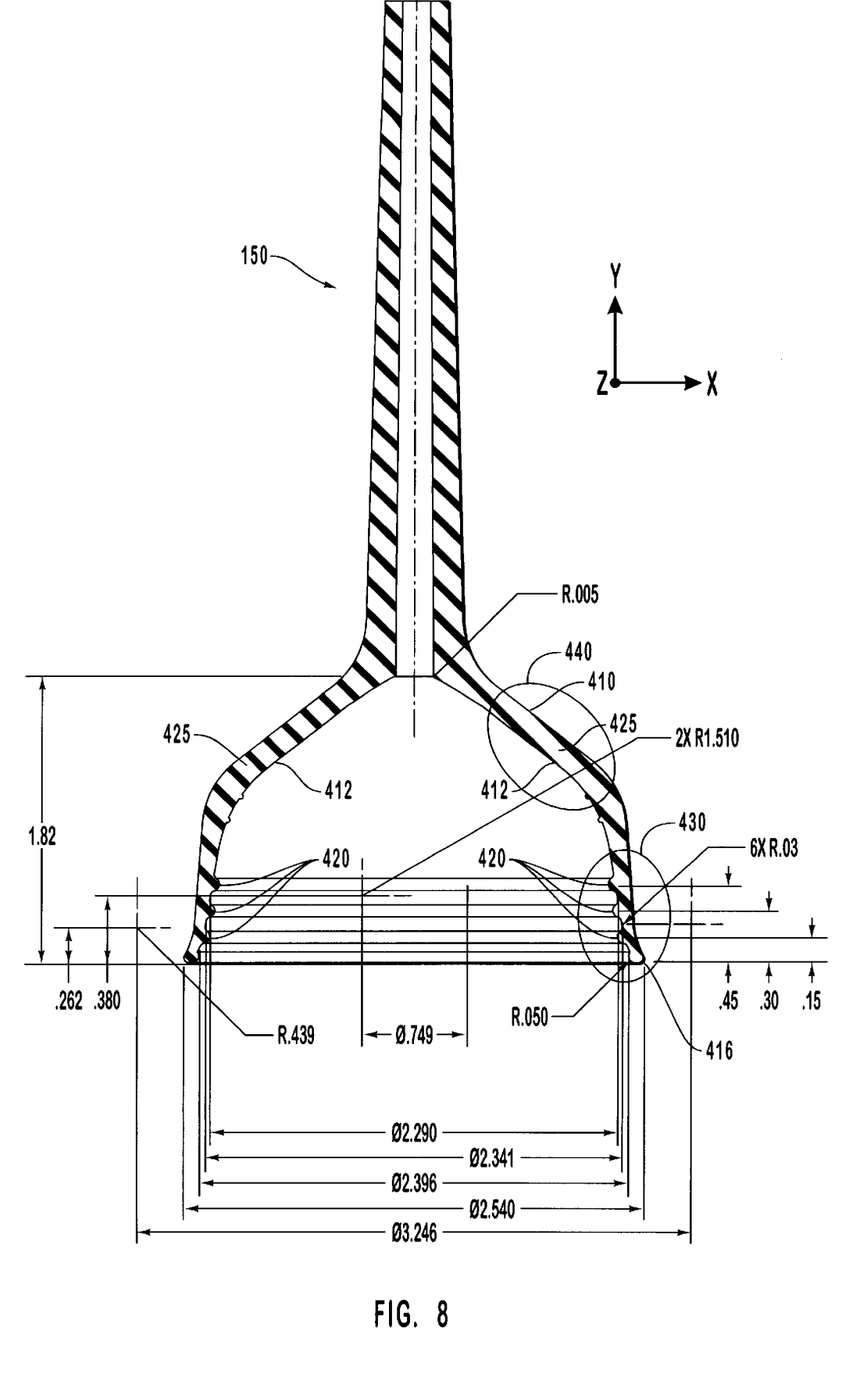
FIG. 8 shows a proportionally correct drawing of the vacuum cup of FIG. 4 with descriptive dimensions shown.

FIG. 8 shows a drawing of the vacuum cup 150 cross section of FIG. 4 with descriptive dimensions. Cup portion 410 has annular ridges 420 circumscribing inner walls 412.

Cup portion 410 has substantially more flexible walls compared to the cups of the prior art. This flexibility is caused by a combination of two factors: the thickness of the walls 425 of cup portion 410 and the elasticity of the materials composing the walls. In one embodiment, the thickness of a ridge region 430 (defined as the region proximate to ridges 420) of walls 425 ranges from 0.010 inches to 0.025 inches or from 0.010 inches to 0.050 inches. In a shaft base region 440 of walls 425, the wall thickness may have a minimum of 0.025 to 0.050 inches and a maximum thickness of from 0.100 to 0.300 inches. This assumes a material having a durometer measurement (an elasticity measurement) of from shore A 20 durometers to shore A 80 durometers. The material may be in the range of shore A 50 to shore A 60 durometers and may be approximately shore A 55 durometers. Such elasticity may be obtained from kraton and silicone. However, more rigid materials may be used if the wall 425 thickness is less. For example, a material twice as rigid will require wall half as thick as those described above.

Figure 9:
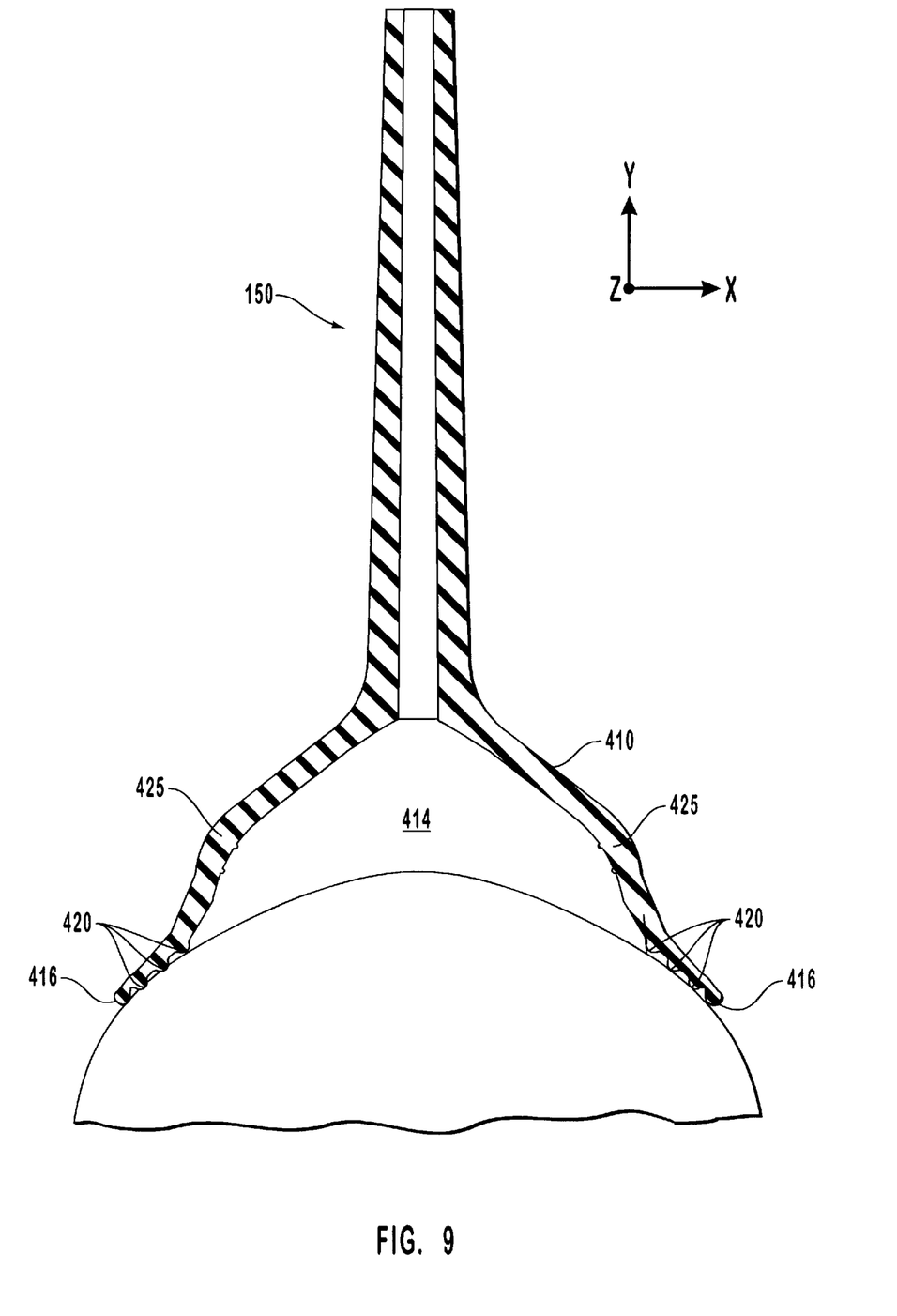
FIG. 9 shows the vacuum cup of FIG. 8 during operation when a vacuum is applied within the cup chamber.

FIG. 9 illustrates vacuum cup 150 during operation when a vacuum is applied within cup chamber 414. In order to apply the cup portion 410, cup portion 410 is slightly compressed onto the fetal head only enough to create a seal between the cup portion 410 and the fetal head H. A vacuum is then applied within cup chamber 414. The vacuum causes urges lip 416 to stretch over the fetal head as the volume within cup chamber 414 decreases, thereby increasing the surface area of the fetal head H exposed to the vacuum. As lip 416 stretches, ridges 420 are also brought in contact with the fetal head H, thereby improving the seal between the fetal head H and cup portion 410. The stretching of lip 416 causes the diameter of the cup chamber 404 at the fetal head to be increased from approximately 2.54 inches to at least approximately 2.80 inches (at least 10%). During operation, this diameter may even increase by 20 to 40% or more.

This increased diameter dramatically increases the fetal head H area exposed to the vacuum. Therefore, the chance of disengagement of the fetal head H decreases, and the amount of possible pulling force increases without increasing the risk of injury to the fetal head H. Even though cup portion 410 has relatively flexible walls, the cup portion 410 does not collapse under a strong vacuum because a portion of the fetal head H is suctioned into cup chamber 414 and supports inner wall 412. The fetal head H is temporarily deformed causing a caput (i.e., a knob-like protrusion) as a portion of the fetal head H is suctioned into the cup chamber 414. However, because cup chamber 414, during operation, is smaller in size than the cup chamber of the prior art, the deformation of the fetal head H is substantially reduced.

Filter 15 (FIG. 1), composed of, for example, a polyester or polyurethane foam, is inserted into cup 3 and adhered to cup 3 with an adhesive. Filter 15 substantially prevents bodily liquids and debris (e.g., vernix, mucus) from entering into handle 1 and palm chamber 2 and interfering with the operation of extractor 100.

A method of operating extractor 100 is described. First, lip 416 of cup portion 410 is attached to a fetal head to define chamber 414. The operating hand is positioned around handle 1 and palm chamber 2 as described above. During a contraction, a vacuum is asserted within chamber 414 by repeating clinching and releasing the operating hand until the desired vacuum is attained. During the contraction and while the desired vacuum is maintained. The operator pulls on handle 1 to draw the fetus through the birth canal. If the vacuum is too high or the mother is between contractions, the vacuum is reduced with vacuum release 130. This whole time, the primary operator can determine the level of vacuum by monitoring vacuum indicator 140.

The above describes a fetal vacuum extractor 100 having a 50 to 75 percent reduction in the sealed off fluid volume compared to the prior art. The "sealed off fluid volume" is defined as "the volume of the fluid to which the vacuum is applied in the extractor." This reduction is due, in part, to the elimination of flexible tubing that is required in the prior art to coupled the remote vacuum pump to the extractor handle. The reduction is also due, in part, to filter 15 occupying volume within cup chamber 414. Furthermore, a single operator can both provide the vacuum and pull on the handle 110 using a single hand. This represents substantial improvements in the art of fetal vacuum extractors.

Figure 6:
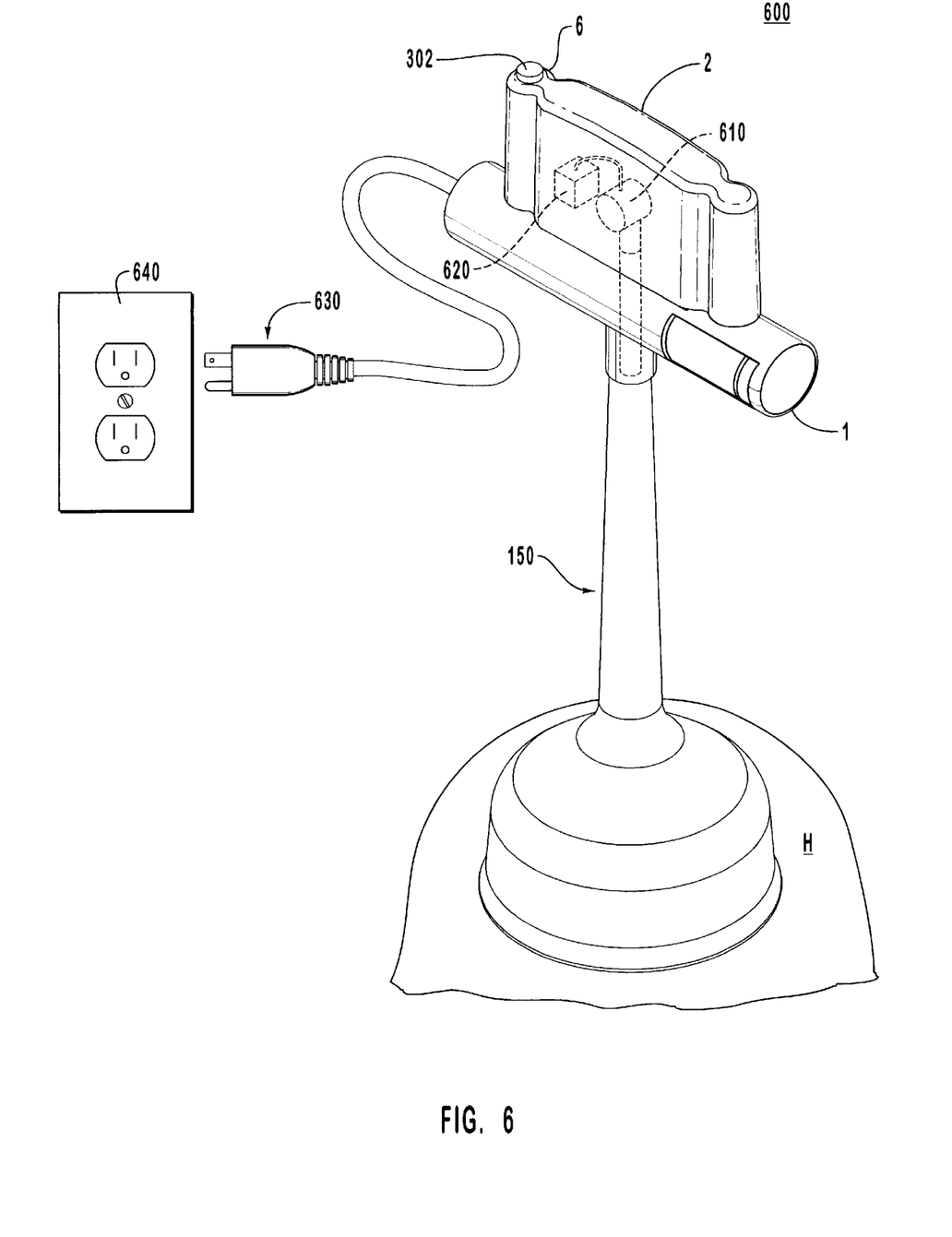
FIG. 6 is an isometric view of another embodiment of the fetal vacuum extractor according to the invention.

There are numerous alternative embodiments that will be apparent to one skilled in the art in light of this description. FIG. 6 is an isometric view of a fetal vacuum extractor 600 according to another embodiment of the invention. Extractor 600 is structured similarly to extractor 100 except that palm chamber 2 is integrated with handle 1 and is electronically operated rather than manually operated. Activation surface 302 is a surface of a button 6.

An electric pump 610 is provided within palm chamber 2, and is activated by pressing a palm or other surface against button 6 to close an electric circuit. Electric pump 610 may be, for example, one of the pumps from the PIAB mini vacuum series which is supplied by PIAB, 65 Sharp Street, Hingham, Mass., 02043. Electric pump 610 is coupled, through cup channel 406, to cup chamber 414 to provide a vacuum in cup chamber 414. The electric pump may be powered by batteries 620 or by an external electricity source such as a plug 630 connected to an outlet 640.

Although specific embodiments have been described, numerous variations of extractors 100 and 600 will be apparent to one skilled in the art as being within the scope of the invention in light of this disclosure.

For example, although valves 8a and 8b are described as being flap valves, valves 8a and 8b may be other types of one-way valves such as a duck bill valve, or a ball valve that has a ball sliding within a seating.

Figure 10:
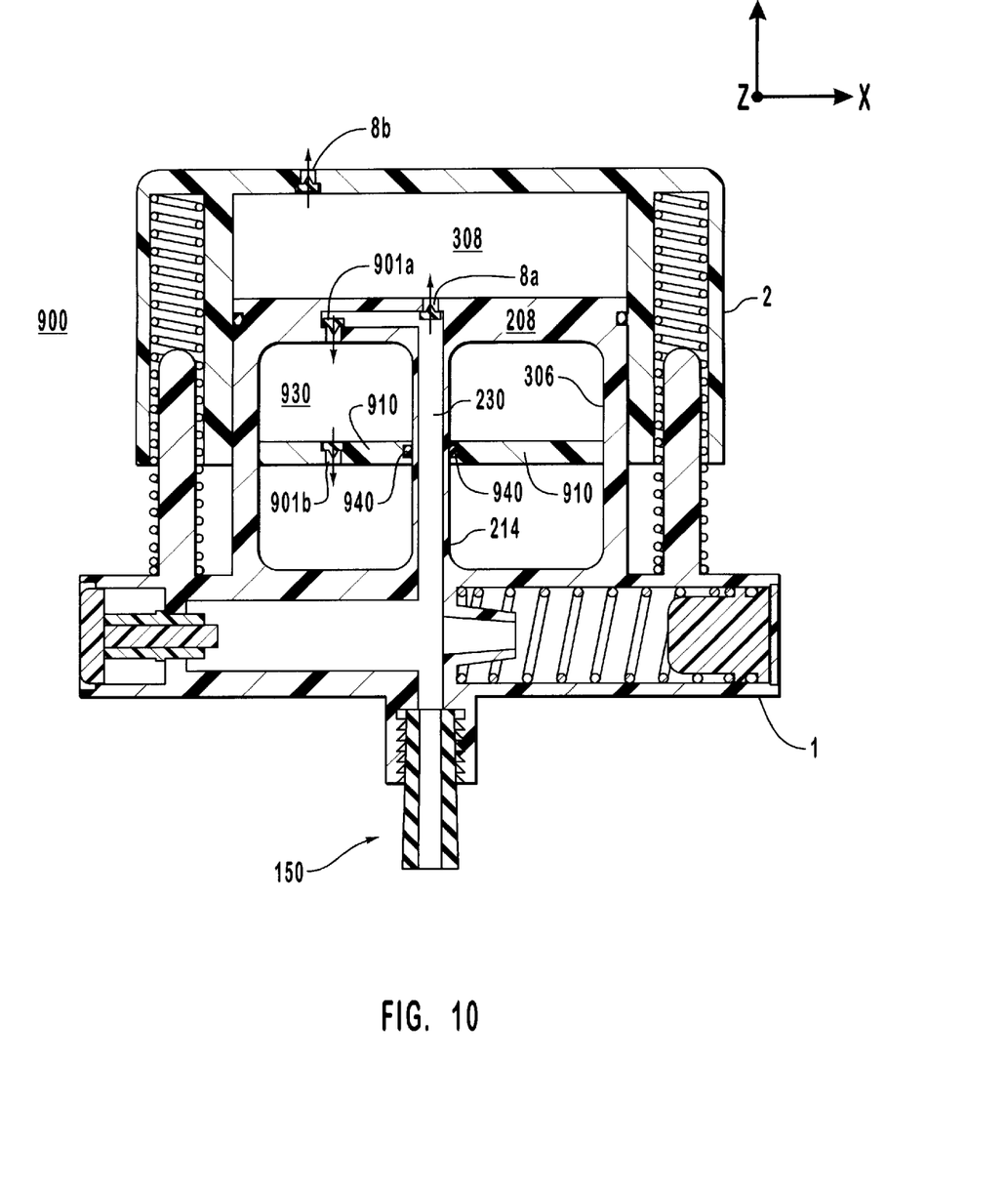
FIG. 10 shows a portion of an extractor which uses four one-way valves instead of two.

FIG. 10 shows a portion of an extractor 900 which is structured similarly to extractor 100 except as follows. Extractor 900 has a secondary vacuum chamber 930 which is defined by inner chamber surface 306, lower surface 238 of piston 208, a lower wall 910 connected to inner chamber surface around central support 214, and an o-ring 940. Valve 8b is provided on through the top of palm chamber 2.

During compression, fluid exhausts from vacuum chamber 308 through valve 8b. As the volume within secondary vacuum chamber 930 increases, fluid is vacuumed from cup chamber 414 (FIG. 4) through a valve 901a coupled to internal vacuum source channel 230. A vacuum is thus created during compression as well. During decompression, fluid exhausts from chamber 930 through valve 901b. Therefore, a vacuum is formed within cup chamber 414 during compression and decompression of palm chamber 2. Therefore, the same vacuum can be created in half the number of pump strokes.

Although vacuum indicator 140 is describes as being composed of a spring loaded o-ring seal or a bellows, other vacuum indicators will suffice such as a vacuum chamber vacuum indicator.

Although a specific pressure release 130, pressure indicator 140 and vacuum cup 150 are described, other vacuum releases, vacuum indicators, and vacuum cups may be used with the fetal vacuum extractor of the present invention. Although a specific structure of handle 1 and palm pump 2 is described, other structures will be apparent in light of this disclosure as being within the principles of this invention. For example, the shape of any of the chambers may be different than described. The rectangular shape described above is ergonomically designed to fit the human hand.

The principles of the present invention apply to extractors that have portions or which are wholly disposable or reusable. For example, vacuum cup 3 may be disposable or the entire extractor 100 may be disposable. On the contrary, palm chamber 2 and handle 1 of extractor 600 may be reusable.

What is claimed is:

1. A fetal vacuum extractor comprising:
   a vacuum cup having a cup portion for application to a fetus, the cup portion defining a cup chamber;
   a handle connected to the vacuum cup, the handle including a grip surface, the handle for maneuvering the vacuum cup; and
   a vacuum pump defining a vacuum chamber fluidly couplable to the cup chamber,
   wherein the vacuum pump includes an activation surface for creating a vacuum in the vacuum chamber,
   wherein the grip surface of the handle and the activation surface of the vacuum pump are in a proximity such that a single human hand can grasp both the grip surface and the activation surface simultaneously,
   wherein compression of the activation surface of the vacuum pump towards the grip surface of the handle reduces the volume within the vacuum chamber.

2. The fetal vacuum extractor of claim 1, wherein the vacuum pump has a chamber surface and a piston surface which define the vacuum chamber.

3. The fetal vacuum extractor of claim 2, wherein the piston surface is rigidly attached to the handle.

4. The fetal vacuum extractor of claim 1, further comprising:
   a one-way vacuum valve coupled between the cup chamber and the vacuum chamber, wherein the one-way vacuum valve opens only if a first pressure at the cup chamber is greater than a second pressure at the vacuum chamber; and
   a one-way exhaust valve coupled between the vacuum chamber and an operating environment, wherein the one-way exhaust valve opens only if the second pressure at the vacuum chamber is greater than an ambient pressure of the operating environment.

5. The fetal vacuum extractor of claim 1, further comprising a vacuum deactivator coupled to the vacuum chamber such that when a vacuum deactivation surface of the vacuum deactivator is contacted, the vacuum chamber is fluidly coupled to an operating environment for releasing a vacuum in the vacuum chamber.

6. The fetal vacuum extractor of claim 5, wherein the vacuum deactivator comprises a vacuum release and the vacuum deactivation surface comprises a surface of a release button of the vacuum deactivator.

7. The fetal vacuum extractor of claim 5, wherein the proximity is such that the single human hand can simultaneously contact the grip surface, the activation surface, and the vacuum deactivation surface during normal operation.

8. The fetal vacuum extractor of claim 7, wherein the vacuum deactivation surface is positioned at a first longitudinal end of the handle.

9. The fetal vacuum extractor of claim 8, further comprising a vacuum gauge provided at a second longitudinal end of the handle opposite the first longitudinal end of the handle.

10. The fetal vacuum extractor of claim 1, further comprising a vacuum gauge provided at a longitudinal end of the handle.

11. The fetal vacuum extractor of claim 1, wherein the vacuum cup is disposable and is low cost.

12. The fetal vacuum extractor of claim 1, wherein the fetal vacuum extractor is entirely disposable and is low cost.

13. The fetal vacuum extractor of claim 1, wherein the vacuum cup further comprises a semi-rigid shaft connecting the handle and cup portion.

14. The fetal vacuum extractor of claim 13, wherein the semi-rigid shaft and the cup portion are molded out of a single piece.

15. The fetal vacuum extractor of claim 1, wherein a lip and an inner wall of the cup portion are stretchable to match a shape of a head of the fetus for a better seal between the head and the cup portion.

16. A fetal vacuum extractor comprising:
    a vacuum cup having a cup portion for application to a fetus, the cup portion defining a cup chamber;
    a handle connected to the vacuum cup, the handle including a grip surface, the handle for maneuvering the vacuum cup; and
    a vacuum pump having at least a portion rigidly connected to the handle, wherein the vacuum pump includes an activation surface for creating a vacuum in the vacuum chamber, wherein the vacuum pump is fluidly coupled to the cup chamber, wherein the grip surface of the handle and the activation surface of the pump are in a proximity, the proximity being such that a single human hand can grasp both the grip surface and the activation surface simultaneously, wherein the vacuum pump has first and second chamber surfaces which define the vacuum chamber, wherein the second chamber surface comprises a surface of a piston, the piston being rigidly attached to the handle, wherein the vacuum pump is slidably movable towards and away from the handle, wherein compression of the activation surface of the vacuum pump towards the grip surface of the handle results in the piston reducing the volume within the vacuum chamber.

17. The fetal vacuum extractor of claim 16, wherein the proximity is between 1 and 5 inches when the fetal vacuum extractor is in an uncompressed position.

18. The fetal vacuum extractor of claim 17, wherein the proximity is approximately 3 inches when the fetal vacuum extractor is in the uncompressed position.

19. The fetal vacuum extractor of claim 18, wherein the proximity is between ½ to 4 inches when the fetal vacuum extractor is in a compressed position.

20. The fetal vacuum extractor of claim 19, wherein the proximity is approximately 2 inches when the fetal vacuum extractor is in the compressed position.

21. The fetal vacuum extractor of claim 16, wherein the vacuum chamber is a primary vacuum chamber, wherein compression of the activation surface of the vacuum pump towards the grip surface of the handle results in the piston increasing the volume within a secondary vacuum chamber, wherein a first one-way vacuum valve is coupled between the cup chamber and the secondary vacuum chamber, the first one-way vacuum valve opening only if a first pressure at the cup chamber is greater than a second pressure at the secondary vacuum chamber, wherein a first one-way exhaust valve is coupled between the secondary vacuum chamber and an operating environment, wherein the first one-way exhaust valve opens only if the second pressure at the secondary vacuum chamber is greater than an ambient pressure of the operating environment.

22. The fetal vacuum extractor of claim 21, further comprising:
    a second one-way vacuum valve coupled between the cup chamber and the primary vacuum chamber, wherein the second one-way vacuum valve opens only if the first pressure at the cup chamber is greater than a third pressure at the primary vacuum chamber; and
    a second one-way exhaust valve coupled between the vacuum chamber and the operating environment, wherein the second one-way exhaust valve opens only if the third pressure at the primary vacuum chamber is greater than the ambient pressure of the operating environment.

23. A fetal vacuum extractor comprising:
a vacuum cup having a cup portion for application to a fetus, the cup portion defining a cup chamber;
a handle connected to the vacuum cup, the handle including a grip surface, the handle for maneuvering the vacuum cup;
a vacuum pump having at least a portion rigidly connected to the handle, wherein the vacuum pump includes an activation surface for creating a vacuum in the cup chamber, wherein the vacuum pump is fluidly coupled to the cup chamber, wherein the grip surface of the handle and the activation surface of the pump are in a proximity, the proximity being such that a single human hand can grasp both the grip surface and the activation surface simultaneously, the fetal vacuum extractor further comprising a filter disposed in the cup portion for preventing liquids and debris from entering the handle.

24. A fetal vacuum extractor comprising:
a vacuum cup having a cup portion for application to a fetus, the cup portion defining a cup chamber;
a handle connected to the vacuum cup, the handle including a grip surface, the handle for maneuvering the vacuum cup;
a vacuum pump having at least a portion rigidly connected to the handle, wherein the vacuum pump includes an activation surface for creating a vacuum in the cup chamber, wherein the vacuum pump is fluidly coupled to the cup chamber, wherein the grip surface of the handle and the activation surface of the pump are in a proximity, the proximity being such that a single human hand can grasp both the grip surface and the activation surface simultaneously, wherein the cup portion has annular ridges disposed along a circumference of an inner wall of the cup portion, the annular ridges for helping to hold the fetus.

25. A fetal vacuum extractor comprising:
a vacuum cup having a cup portion for application to a fetus, the cup portion defining a cup chamber;
a handle connected to the vacuum cup, the handle including a grip surface, the handle for maneuvering the vacuum cup; and
a vacuum pump defining a vacuum chamber fluidly couplable to the cup chamber,
wherein the vacuum pump includes an activation surface for creating a vacuum in the vacuum chamber,
wherein the grip surface of the handle and the activation surface of the pump are in a proximity such that a single human hand can grasp both the grip surface and the activation surface simultaneously, and
wherein the vacuum cup further comprises a semi-rigid shaft connecting the handle and cup portion.

26. The fetal vacuum extractor of claim 25, wherein the semi-rigid shaft and the cup portion are molded out of a single piece.

27. A fetal vacuum extractor comprising:
a vacuum cup having a cup portion for application to a fetus, the cup portion defining a cup chamber;
a handle connected to the vacuum cup, the handle including a grip surface, the handle for maneuvering the vacuum cup; and
a vacuum pump defining a vacuum chamber fluidly couplable to the cup chamber, wherein the vacuum pump includes an activation surface for creating a vacuum in the vacuum chamber; and
a vacuum deactivator coupled to the vacuum chamber such that when a vacuum deactivation surface of the vacuum deactivator is contacted, the vacuum chamber is fluidly coupled to an operating environment for releasing a vacuum in the vacuum chamber,
wherein the grip surface of the handle, the activation surface of the pump, and the vacuum deactivation surface of the vacuum deactivator are in a proximity such that a single human hand can grasp the grip surface, the activation surface, and the vacuum deactivation surface simultaneously.

28. The fetal vacuum extractor of claim 27, wherein the vacuum deactivation surface is positioned at a first longitudinal end of the handle.

29. The fetal vacuum extractor of claim 28, further comprising a vacuum gauge provided at a second longitudinal end of the handle opposite the first longitudinal end of the handle.

30. A fetal vacuum extractor comprising:
a vacuum cup having a cup portion for application to a fetal head, the cup portion having inner walls defining a cup chamber, the cup portion having lips for contacting the fetus, the cup portion structured such that the lips stretch out over the fetal head when a vacuum is applied within the cup chamber, the lips stretching to increase the diameter of the cup portion by at least 10%;
a handle connected to the vacuum cup, the handle including a grip surface, the handle for maneuvering the vacuum cup; and
a vacuum pump defining a vacuum chamber fluidly couplable to the cup chamber,
wherein the vacuum pump includes an activation surface for creating a vacuum in the vacuum chamber,
wherein the grip surface of the handle and the activation surface of the pump are in a proximity such that a single human hand can grasp both the grip surface and the activation surface simultaneously.

31. The fetal vacuum cup of claim 30, wherein the cup portion has a wall having a ridge region composed of a material having an elasticity of from shore A 20 durometers to shore A 80 durometers, the material having a maximum thickness of 0.050 inches or less.

32. The fetal vacuum cup of claim 31, wherein the maximum thickness is 0.025 inches or less.

33. A fetal vacuum extractor comprising:
a vacuum cup having a cup portion for application to a fetus, the cup portion defining a cup chamber;
a handle connected to the vacuum cup, the handle including a grip surface, the handle for maneuvering the vacuum cup; and
a vacuum pump defining a vacuum chamber fluidly couplable to the cup chamber,
wherein the vacuum pump includes an activation surface for creating a vacuum in the vacuum chamber,
wherein the grip surface of the handle and the activation surface of the pump are in a proximity such that a single human hand can grasp both the grip surface and the activation surface simultaneously, and
wherein compression of the activation surface of the vacuum pump towards the grip surface of the handle reduces the volume within the vacuum chamber.

34. A fetal vacuum extractor comprising:

a vacuum cup having a cup portion for application to a fetus, the cup portion defining a cup chamber;

a handle connected to the vacuum cup, the handle including a grip surface, the handle for maneuvering the vacuum cup;

a filter disposed in the cup portion for preventing liquids and debris from entering the handle; and a vacuum pump defining a vacuum chamber fluidly couplable to the cup chamber, wherein the vacuum pump includes an activation surface for creating a vacuum in the vacuum chamber, and wherein the grip surface of the handle and the activation surface of the pump are in a proximity such that a single human hand can grasp both the grip surface and the activation surface simultaneously.

35. A fetal vacuum extractor comprising:

a vacuum cup having a cup portion for application to a fetus, the cup portion defining a cup chamber;

a handle connected to the vacuum cup, the handle including a grip surface, the handle for maneuvering the vacuum cup; and a vacuum pump defining a vacuum chamber fluidly couplable to the cup chamber, wherein the vacuum pump includes an activation surface for creating a vacuum in the vacuum chamber, wherein the grip surface of the handle and the activation surface of the pump are in a proximity such that a single human hand can grasp both the grip surface and the activation surface simultaneously, and wherein the cup portion has annular ridges disposed along a circumference of an inner wall of the cup portion, the annular ridges for helping to hold the fetus.

* * * * *

UNITED STATES PATENT AND TRADEMARK OFFICE
CERTIFICATE OF CORRECTION

PATENT NO. : 6,074,399  
APPLICATION NO. : 09/075448  
DATED : June 13, 2000  
INVENTOR(S) : William Dean Wallace et al.

Page 1 of 1

It is certified that error appears in the above-identified patent and that said Letters Patent is hereby corrected as shown below:

In the specification:
| | | |
|---|---|---|
| COLUMN 3, | LINE 1, | after "diagram" and before "the" insert --of-- |
| COLUMN 7, | LINE 14, | after "vacuum" delete "causes" |
| COLUMN 7, | LINE 65, | change "coupled" to --couple-- |
| COLUMN 8, | LINE 48, | change "describes" to --describes-- |

In the claims:
| | | | |
|---|---|---|---|
| CLAIM 23, | COLUMN 11, | LINE 16, | before "pump" insert --vacuum-- |
| CLAIM 24, | COLUMN 11, | LINE 34, | before "pump" insert --vacuum-- |
| CLAIM 25, | COLUMN 11, | LINE 52, | before "pump" insert --vacuum-- |
| CLAIM 25, | COLUMN 11, | LINE 56, | before "cup" insert --the-- |
| CLAIM 27, | COLUMN 12, | LINE 11, | before "pump" insert --vacuum-- |
| CLAIM 30, | COLUMN 12, | LINE 40, | before "pump" insert --vacuum-- |
| CLAIM 33, | COLUMN 12, | LINE 62, | before "pump" insert --vacuum-- |
| CLAIM 34, | COLUMN 13, | LINE 14, | before "pump" insert --vacuum-- |
| CLAIM 35, | COLUMN 14, | LINE 12, | before "pump" insert --vacuum-- |

Signed and Sealed this

Twenty-second Day of August, 2006

JON W. DUDAS  
*Director of the United States Patent and Trademark Office*